US010976148B2

(12) United States Patent
Racheli et al.

(10) Patent No.: US 10,976,148 B2
(45) Date of Patent: Apr. 13, 2021

(54) CALIBRATION JIG FOR A CATHETER COMPRISING A POSITION SENSOR

(71) Applicant: Biosense Webster (Israel) Ltd., Yokneam (IL)

(72) Inventors: Noam Racheli, Hadera (IL); Itamar Bustan, Zichron Ya'acov (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 187 days.

(21) Appl. No.: 15/980,625

(22) Filed: May 15, 2018

(65) Prior Publication Data
US 2019/0353471 A1    Nov. 21, 2019

(51) Int. Cl.
   *G01B 7/14*   (2006.01)
   *A61B 5/06*   (2006.01)
   *A61M 25/01*  (2006.01)

(52) U.S. Cl.
   CPC .............. *G01B 7/14* (2013.01); *A61B 5/062* (2013.01); *A61M 25/0127* (2013.01); *A61B 2560/0223* (2013.01); *A61M 2025/0166* (2013.01); *A61M 2205/70* (2013.01)

(58) Field of Classification Search
   CPC . G01B 7/14; A61M 25/0127; A61M 2205/70; A61M 2025/0166; A61B 5/062; A61B 2560/0223; A61B 5/6852; A61B 5/6869; A61B 2034/2051; A61B 34/20
   See application file for complete search history.

(56) References Cited

U.S. PATENT DOCUMENTS

| 5,391,199 A | 2/1995 | Ben-Haim |
| 6,239,724 B1 | 5/2001 | Doron et al. |
| 6,266,551 B1 | 7/2001 | Osadchy et al. |
| 6,332,089 B1 | 12/2001 | Acker et al. |
| 6,484,118 B1* | 11/2002 | Govari .................... A61B 5/06 |
| | | 702/150 |
| 6,585,118 B2 | 7/2003 | Kellogg |
| 6,618,612 B1 | 9/2003 | Acker et al. |
| 6,690,963 B2 | 2/2004 | Ben-Haim et al. |
| 8,798,952 B2* | 8/2014 | Govari ................ A61B 5/1495 |
| | | 702/101 |

(Continued)

FOREIGN PATENT DOCUMENTS

| EP | 1952768 | 8/2008 |
| WO | WO 9605768 | 2/1996 |

OTHER PUBLICATIONS

European Search Report dated Oct. 11, 2019 from corresponding European Patent Application No. 19174449.9.

*Primary Examiner* — Nimeshkumar D Patel
*Assistant Examiner* — Gedeon M Kidanu
(74) *Attorney, Agent, or Firm* — Frost Brown Todd LLC

(57) ABSTRACT

An apparatus includes a calibration fixture, a calibration position sensor, and interface circuitry. The calibration fixture is sized and shaped to fit over a distal-end of a medical probe, such that the distal-end makes physical contact with a wall of the calibration fixture. The calibration position sensor is fixed in the calibration fixture at a known position relative to the wall, and configured, in response to sensing a magnetic field, to produce position signals indicative of a given position of the calibration position sensor. The interface circuitry is electrically coupled to the calibration position sensor, and is configured to output the position signals.

20 Claims, 2 Drawing Sheets

(56) References Cited

U.S. PATENT DOCUMENTS

| | | |
|---|---|---|
| 2001/0027271 A1 | 10/2001 | Franck et al. |
| 2002/0065455 A1 | 5/2002 | Ben-Haim et al. |
| 2003/0120150 A1 | 6/2003 | Govari |
| 2004/0068178 A1* | 4/2004 | Govari .................. A61B 90/10 600/424 |
| 2004/0254458 A1 | 12/2004 | Govari |
| 2007/0106156 A1* | 5/2007 | Altmann ................. A61B 8/12 600/437 |
| 2008/0183075 A1* | 7/2008 | Govari .................... A61B 8/12 600/437 |
| 2011/0153253 A1* | 6/2011 | Govari ................ A61B 5/1495 702/98 |
| 2011/0307207 A1* | 12/2011 | Govari ................ A61B 5/1495 702/98 |
| 2013/0066193 A1* | 3/2013 | Olson ................... A61B 5/062 600/424 |
| 2014/0095105 A1* | 4/2014 | Koyrakh ................ G01C 21/00 702/152 |
| 2014/0114173 A1* | 4/2014 | Bar-Tal ................ A61B 5/0522 600/409 |
| 2014/0275998 A1* | 9/2014 | Eichler .................. A61B 6/586 600/424 |
| 2015/0247944 A1 | 9/2015 | Govari et al. |

* cited by examiner

CALIBRATION JIG FOR A CATHETER COMPRISING A POSITION SENSOR

FIELD OF THE INVENTION

The present invention relates generally to medical devices, and particularly to methods and systems for calibrating a catheter comprising a position sensor.

BACKGROUND OF THE INVENTION

Position sensors are used, inter alia, for tracking medical devices in a patient body. Various techniques for calibrating and applying such devices and sensors are known in the art.

For example, U.S. Patent Application Publication 2015/0247944, issued as U.S. Pat. No. 9,638,820 on May 2, 2017, describes a calibration jig for a flat location pad. The jig includes a detector assembly, a positioning unit, and interface circuitry. The detector assembly includes an array of multiple magnetic field detectors. The positioning unit is configured to fix the detector assembly at one or more known positions relative to a location pad. The interface circuitry is configured to output electrical signals that are produced by the magnetic field detectors of the detector assembly when the detector assembly is fixed at the known positions, so as to calibrate the position measurements performed by the positioning system.

U.S. Patent Application Publication 2001/0027271, issued as U.S. Pat. No. 6,298,262 on Oct. 2, 2001, describes a method and apparatus for positioning a surgical instrument during stereotactic surgery using a guidance fixture. The guidance fixture includes an upper portion, which includes an instrument guide for moving the surgical instrument along a constrained trajectory relative to the upper portion, and includes an adjustable base supporting the upper portion, which includes a mounting base and an adjustment mechanism.

SUMMARY OF THE INVENTION

An embodiment of the present invention that is described herein provides an apparatus that includes a calibration fixture, a calibration position sensor, and interface circuitry. The calibration fixture is sized and shaped to fit over a distal-end of a medical probe, such that the distal-end makes physical contact with a wall of the calibration fixture. The calibration position sensor is fixed in the calibration fixture at a known position relative to the wall, and configured, in response to sensing a magnetic field, to produce position signals indicative of a given position of the calibration position sensor. The interface circuitry is electrically coupled to the calibration position sensor, and is configured to output the position signals.

In some embodiments, the apparatus includes a processor, which is configured to: (i) receive electrical signals indicative of a measured position of a probe position sensor attached to the medical probe, (ii) receive the position signals produced by the calibration position sensor, and (iii) estimate, based on the electrical signals and the position signals, a distance between the probe position sensor and a tip of the distal end. In other embodiments, the apparatus includes an additional calibration position sensor, fixed in the calibration fixture at a predefined position relative to the calibration position sensor, and configured, in response to sensing the magnetic field, to produce additional position signals indicative of an additional position of the additional calibration position sensor. The processor is further configured to produce, based on the predefined position, the position signals and the additional position signals, a scaling factor for estimating the distance.

In an embodiment, the apparatus includes a calibration appliance, which is fixed to the calibration fixture and is configured to produce the magnetic field. In another embodiment, the calibration appliance includes multiple Helmholtz coils, which are configured to produce the magnetic field. In yet another embodiment, the interface circuitry is configured to transmit the position signals wirelessly or via an electrical cable coupled to the interface circuitry.

There is additionally provided, in accordance with an embodiment of the present invention, a method for producing a calibration apparatus, the method includes producing a calibration fixture, sized and shaped to fit over a distal-end of a medical probe, such that the distal-end makes physical contact with a wall of the calibration fixture. A calibration position sensor, for producing position signals that are indicative of a given position of the calibration position sensor in response to sensing a magnetic field, is fixed in the calibration fixture at a known position relative to the wall. Interface circuitry for outputting the position signals is electrically coupled to the calibration position sensor.

The present invention will be more fully understood from the following detailed description of the embodiments thereof, taken together with the drawings in which:

DETAILED DESCRIPTION OF EMBODIMENTS

Overview

Figure 1:
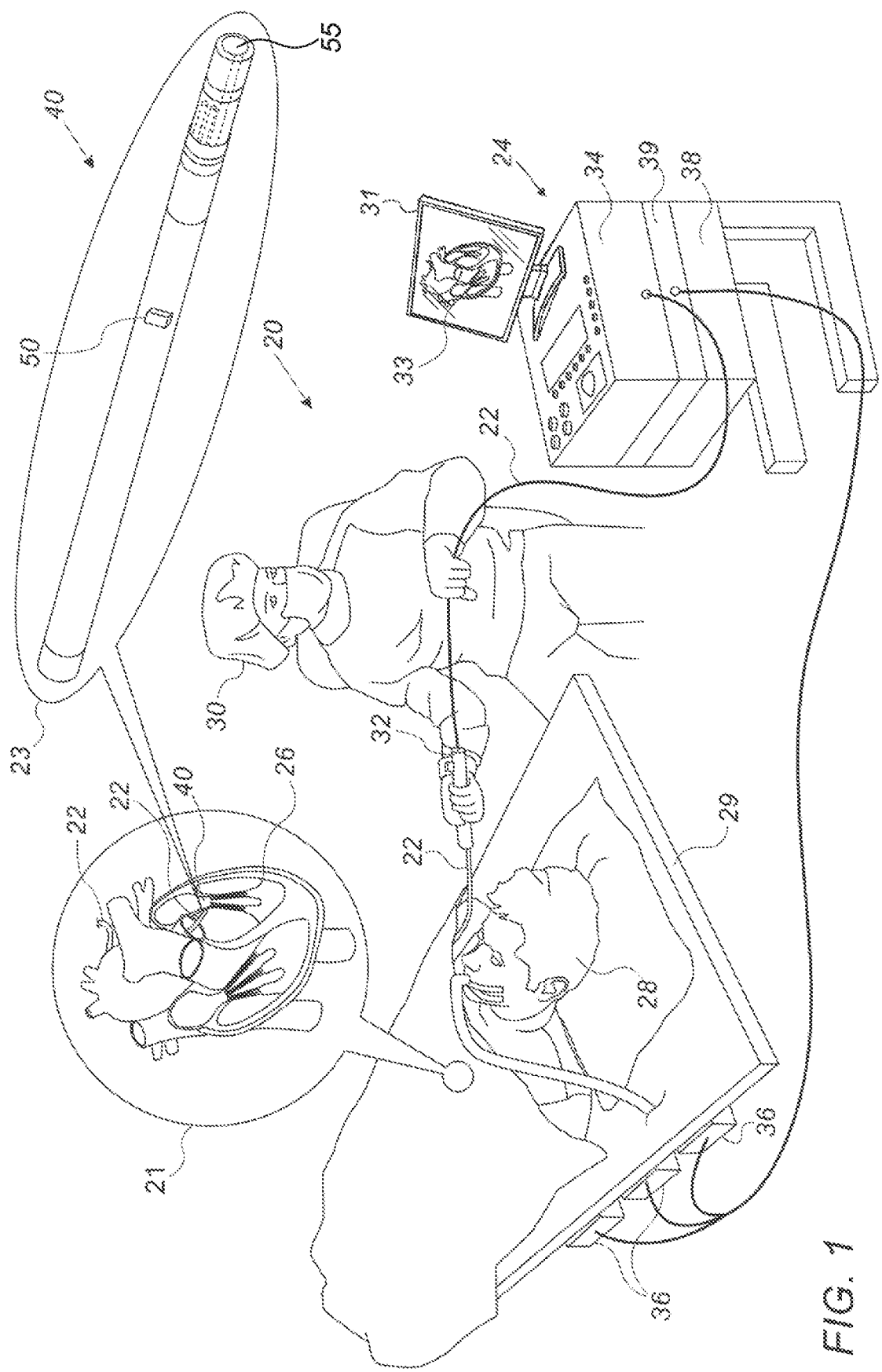
FIG. 1 is a schematic, pictorial illustration of a catheterization system, in accordance with an embodiment of the present invention.

Minimally invasive medical devices, such as a cardiac catheter, may comprise at least one position sensor coupled thereto at a given location. The actual location of the position sensor relative to the catheter distal tip may differ even among multiple catheters of the same type, for example, due to inaccuracies in the production process. An error in the location of the position sensor on the catheter may result in estimation error of the position of the catheter distal-end.

In principle, calibration of the catheter may be carried out by placing the catheter in a jig, which is located inside a Helmholtz chamber. Prior to calibrating the catheter, the jig has to be registered with the chamber, typically by applying a known magnetic field on a pre-calibrated testing catheter and measuring an output voltage produced by the testing catheter. At production, any changes related to the jig typically require re-registration between the jig and the chamber, which is time consuming and increases production costs. Events that require re-registration include, for example, a movement of jig within the chamber, and replacing the jig to a different type suitable for use in a different type of catheter.

Embodiments of the present invention that are described hereinbelow provide improved techniques for calibrating a catheter comprising a position sensor, by accurately evaluating the distance between the position sensor and the distal tip of the catheter. The calibration enables accurate tracking of the catheter distal-end.

In some embodiments, a calibration jig comprises a fixture that is sized and shaped to fit over a distal-end of the catheter. The fixture has an opening that extends to a hole in the fixture bulk, such that the distal-end of the catheter is inserted through the opening and makes a physical contact with a wall located at the end of the hole in the fixture bulk.

In some embodiments, the jig comprises one or more calibration position sensors. Consider a first calibration position sensor, fixed in the fixture at a known distance from the wall. In some embodiments, the jig is fixed in a calibration chamber comprising three pairs of Helmholtz coils, or any other type of suitable coils. The coils of each pair are positioned at a predefined distance parallel to one another, and the pairs are positioned orthogonal to one another. In this configuration, by applying suitable electrical currents through the coils, the coils are configured to produce a magnetic field in a predefined inner volume formed within the coils.

In some embodiments, first the calibration position sensor is configured to produce, in response to sensing the magnetic field, position signals indicative of a given position of the calibration position sensor. In some embodiments, the calibration jig further comprises interface circuitry, which is electrically coupled to the calibration position sensor, and is configured to output the position signals, e.g., to a processor of a control console of the calibration chamber.

In some embodiments, during calibration, the distal-end is inserted through the opening and makes physical contact with the wall, whereas the proximal end of the catheter is electrically coupled to the control console for sending to the console the position signals. Subsequently, the calibration chamber is activated to produce the magnetic field, as described above, to produce the magnetic field.

In response to sensing the magnetic field, the position sensor of the catheter and the calibration position sensor of the jig produce position signals indicative of the respective positions of the catheter position sensor and the calibration position sensor.

In some embodiments, the processor of the console estimates, based on the position signals, a total distance between the catheter position sensor and the calibration position sensor. The processor subtracts the known distance (i.e., the distance between the calibration position sensor and the wall) from the estimated total distance, so as to calculate the distance between the catheter position sensor and the tip of the distal-end, which is in physical contact with the wall. The processor stores this calculated distance in a memory device embedded in the catheter, for example, as a variable in a catheter calibration file.

In other embodiments, the jig comprises a second calibration position sensor, fixed at a known distance from the first calibration position sensor. The second calibration position sensor is configured to produce, in response to sensing the magnetic field described above, position signals indicative of the position of the second calibration position sensor. In these embodiments, based on the positions of the first and second calibration position sensors, and on the known distance therebetween, the processor is configured to produce a scaling factor that converts a field gradient of the magnetic field formed between the first and second calibration position sensors, into a distance value, e.g., in units of millimeters. The processor may use the scaling factor to improve the accuracy in estimating the distance between the catheter position sensor and the tip of the distal-end.

The disclosed techniques improve the accuracy of position tracking systems and may reduce the cycle time of the medical procedure by pre-calibrating each catheter used in conjunction with the position tracking system. Furthermore, the disclosed techniques reduce the need to re-register between the jig and the chamber, thereby improving production efficiency and reducing the costs of producing such medical devices.

System Description

FIG. 1 is a schematic, pictorial illustration of a catheterization system 20, in accordance with an embodiment of the present invention. System 20 comprises a probe, in the present example a cardiac catheter 22, and a control console 24. In the embodiment described herein, catheter may be used for any suitable therapeutic and/or diagnostic purposes, such as mapping of electro-cardiac signals for the diagnosis of cardiac dysfunctions, e.g., cardiac arrhythmias.

Console 24 comprises a processor 34, typically a general-purpose computer, with suitable front end and interface circuits for receiving signals from catheter 22 and for controlling the other components of system 20 described herein. Processor 34 may be programmed in software to carry out the functions that are used by the system, and the processor stores data for the software in a memory 38. The software may be downloaded to console 24 in electronic form, over a network, for example, or it may be provided on non-transitory tangible media, such as optical, magnetic or electronic memory media. Alternatively, some or all of the functions of processor 34 may be carried out by dedicated or programmable digital hardware components.

An operator 30 (such as an interventional cardiologist) inserts catheter 22 through the vascular system of a patient 28 lying on a table 29. Catheter 22 comprises an insertion tube, and a distal-end assembly 40 that comprises one or more position sensors 50 shown in an inset 23. Operator 30 moves assembly 40 of catheter 22 in the vicinity of the target region in heart 26 by manipulating catheter 22 with a manipulator 32 near the proximal end of the catheter as shown in an inset 21. The proximal end of catheter 22 is connected to interface circuitry in processor 34.

In some embodiments, system 20 comprises a magnetic position tracking system. The position of distal-end assembly 40 in the heart cavity is typically measured using one or more magnetic position sensors of the magnetic position tracking system. In the example of FIG. 1, console 24 comprises a driver circuit 39, which drives magnetic field generators 36 placed at known positions external to patient 28 lying on table 29, e.g., below the patient's torso.

Reference is now made to inset 23. Distal-end assembly 40 typically comprises one or more position sensors 50 and other devices coupled thereto, such as mapping electrodes (not shown). When the distal-end assembly is brought into contact with the inner surface of heart 26, the mapping electrodes generate potential gradient signals in response to the sensed electrical potentials and position sensors 50 generate position signals in response to the sensed external magnetic fields, thereby enabling processor 34 to map the electrical potentials as a function of position within the heart cavity.

The multiple position sensors and mapping electrodes in assembly 40 are connected to interface circuitry in processor 34 at the catheter proximal end. Operator 30 can view the position of assembly 40 in an image 33 of heart 26 on a user display 31.

This method of position sensing is implemented in magnetic position tracking systems, for example in the CARTO™ system, produced by Biosense Webster Inc. (Irvine, Calif.) and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, issued as U.S. Pat. No. 6,690,963 on Feb. 10, 2004, 2003/0120150 A1, issued as U.S. Pat. No. 7,729,742 on Jun. 1, 2010, and 2004/0068178 A1, now abandoned, whose disclosures are all incorporated herein by reference.

In some embodiments, processor 34 holds a value indicative of the distance between position sensor 50 and a tip 55 of distal end assembly 40. Based on the position signals received from sensor 50 and on the distance value, processor 34 is configured to estimate the position of tip 55 in heart 40.

The specific configuration shown in FIG. 1 is depicted purely by way of example. In alternative embodiments, system 20 may operate in conjunction with any other suitable components and modules. For example, position sensor 50 may comprise a triple-axis sensor (TAS) having three coils, or alternatively, may comprise a single axis sensor (SAS) having a single coil. The position sensor may be formed by disposing the coils on a flexible substrate coupled to catheter 22, or by mounting a device comprising the coils on distal end assembly 40, or using any other suitable configuration and production techniques.

Calibrating the Distance Between Catheter Position Sensor and Distal Tip

Figure 2:
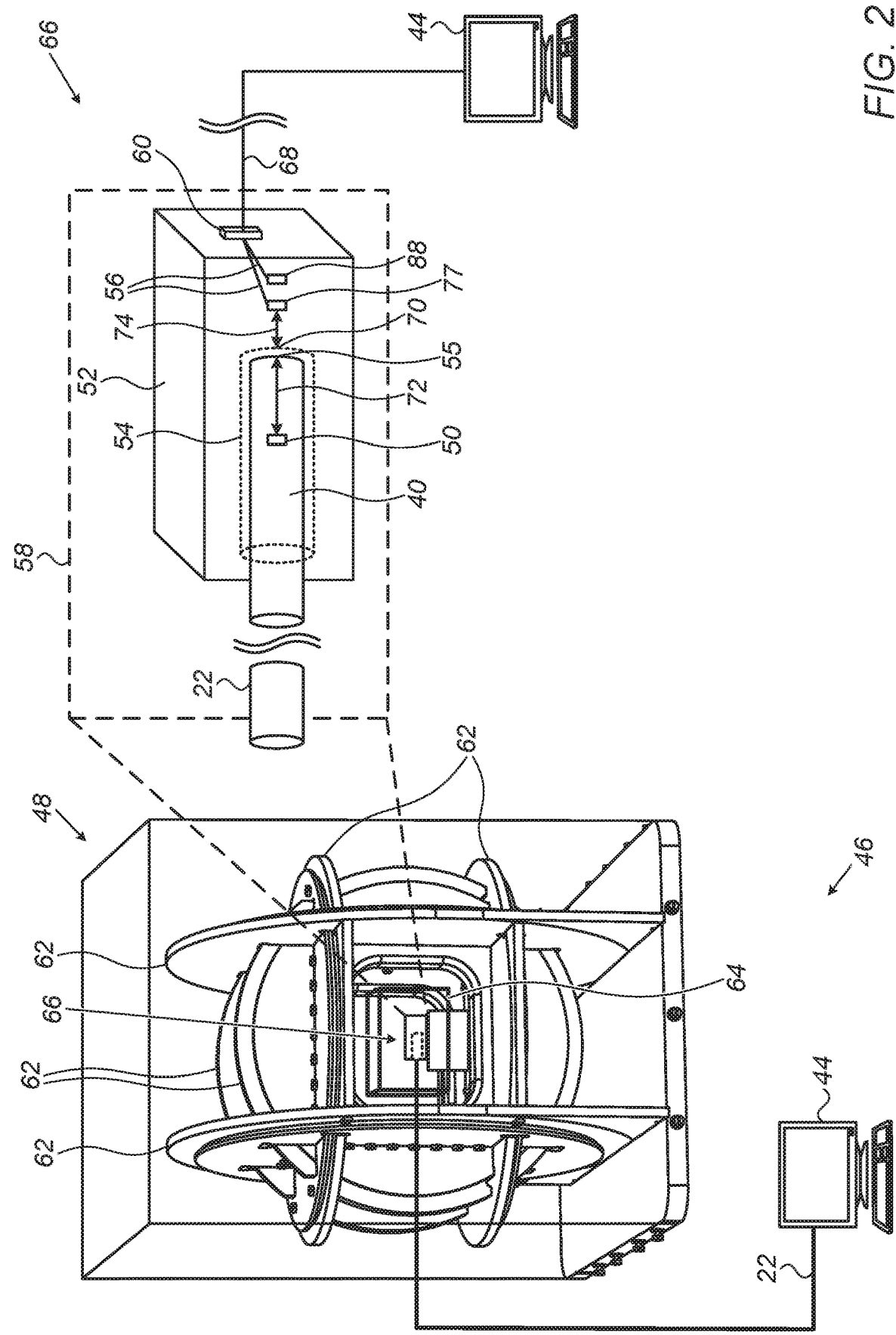
FIG. 2 is a schematic, pictorial illustration of a calibration appliance, in accordance with an embodiment of the present invention.

FIG. 2 is a schematic, pictorial illustration of a calibration appliance 46, in accordance with an embodiment of the present invention. In some embodiments, appliance 46 is configured to output a value indicative of the distance between position sensor 50 and tip 55.

In the example of FIG. 1, the value is stored in a memory device of catheter 22, for example in a memory device embedded in catheter 22 and in a central database of the catheter manufacturer. In an embodiment, the memory device stores additional calibration parameters applied during the catheterization procedure, so as to improve the accuracy in tracking the position of tip 55 in heart 40. Note that due to limited manufacturing accuracy, the distance between the position sensor and the tip may vary among catheters of the same type. Therefore, this distance should be obtained for each catheter separately, e.g., using the calibration jig, and used, before the catheterization procedure, for calibrating system 20.

In some embodiments, appliance 46 comprises a calibration chamber 48 and a control console 44, which comprises a processor (not shown). Chamber 48 comprises three pairs of Helmholtz coils, wherein the pairs are arranged orthogonally to one another. Each pair of coils comprises two substantially similar circular coils 62 made from insulated solid wires placed at a predefined distance parallel to one another aligned to a common axis. Circular coils 62 carry substantially similar respective electrical currents flowing in the same direction. Each pair of coils is configured to create a magnetic field within a volume between the two coils, across the respective axis. The electrical current is adjustable (e.g., by controlling the voltage or current applied to coils 62) and the magnitude of the induced magnetic field is proportional to the applied current.

In some embodiments, by applying similar currents to all of the six coils 62 simultaneously, chamber 48 is configured to produce a magnetic field across a cube 64 mounted therebetween. In some embodiments, cube 64 is made from non-magnetic materials, such as glass, or comprises an open frame, and serves as a calibration volume of chamber 48.

During calibration, the sensitivity of sensor 50 is determined by applying a known magnetic field, e.g., 0.1 gauss, and, in response to the applied magnetic field, measuring the voltage output from sensor 50, e.g., 5 volts. The volts/gauss ratio determines the sensitivity of sensor 50, also referred to herein as "conversion factor." Note that the voltage is a linear function of the magnetic field, such that increasing the applied magnetic field by 10% will result in 10% higher voltage output from sensor 50. The conversion factor of sensor 50 is also stored in the memory device of catheter 22.

In some embodiments, appliance 46 comprises a calibration fixture, referred to herein as a calibration jig 66, which is fixed in cube 64 during the calibration procedure so as to estimate the distance between position sensor 50 and tip 55, as will be described in detail hereinbelow.

Reference is now made to an inset 58, which is a schematic pictorial illustration of calibration jig 66. In some embodiments, calibration jig 66 is sized and shaped to fit over distal-end 40 of catheter 22. In an example embodiment, jig 66 comprises a fixture 52 made from a non-magnetic material such as polycarbonate and having an opening that extends as a hole 54 into the bulk of fixture 52.

In the present example, as depicted in inset 58, hole 54 is sized and shaped to fit over distal-end 40 of catheter 22, such that tip 55 of distal-end 40 makes a physical contact with a wall 70 of hole 54. Note that the diameter of hole 54 is typically slightly larger than the diameter of distal-end 40, so as to allow minimal motion of distal-end 40 within the hole.

In some embodiments, calibration jig 66 comprises one or more calibration position sensors 77 and 88, referred to herein as "calibration sensors" or simply as "sensors" for brevity. In an embodiment, sensors 77 and 88 are magnetic position sensors configured to operate in the magnetic position tracking system described in FIG. 1 above.

Note that the process of measuring the sensitivity of sensor 50 as described above, is also carried out similarly for sensors 77 and 88, such that the voltage/gauss ratios measured for sensors 77 and 88, determine the respective sensitivities of sensors 77 and 88.

In an embodiment, sensors 77 and 88 are fixed in fixture 52 at known positions relative to wall 70. In the example of FIG. 2, calibration position sensor 77 is fixed at a given distance 74 from wall 70, and sensor 88 is fixed at a known position relative to sensor 77.

In an embodiment, position sensors 77 and 88 are configured to produce, in response to sensing a magnetic field applied by coils 62, position signals indicative of their respective positions.

In some embodiments, calibration jig 66 further comprises interface circuitry 60, which is electrically coupled, via respective leads 56, to calibration position sensors 77 and 88. Circuitry 60 is configured to output (e.g., transmit) the position signals produced by sensors 77 and 88, routed via an electrical cable 68, to console 44. In other embodiments, circuitry 60 may comprise a wireless communication device (not shown) configured to wirelessly transmit the position signals of sensors 77 and 88 to console 44.

Note that sensor 88, which is fixed at a known position relative to sensor 77, may assist in estimating the distance between sensor 50 and tip 55, but is not mandatory for the operation of calibration jig 66 in appliance 46. The inventor found that, based on the known distance between sensors 77 and 88, the processor of console 44 can derive a scaling factor that can be used for converting a field gradient of the magnetic field between these sensors into a distance in millimeters.

In the embodiments that will be described below, calibration jig 66 comprises a single calibration position sensor, e.g., sensor 77, but these embodiments are also applicable in a configuration that applies both sensors 77 and 88.

In some embodiments, an operator or a robotic arm (neither shown) inserts distal-end assembly 40 of catheter 22 into hole 54, such that assembly 40 makes a physical contact with wall 70. As shown in FIG. 2, the proximal end of catheter 22 is connected to console 44. Subsequently, the operator applies electrical currents to coils 62 so as to produce a desired magnetic field in cube 64. In response to the magnetic field, position sensor 50 and calibration position sensor 77 respectively produce position signals and calibration position signals, indicative of their respective positions, and send these signals, via catheter 22 and cable 68, to console 44, respectively.

In some embodiments, based on these signals, the processor of console 44 is configured to estimate the distance between sensors 50 and 77. The processor is further configured to calculate a distance 72 between sensor 50 and tip 55, by subtracting given distance 74 from the distance between sensors 50 and 77, which is a sum of distances 72 and 74. As described above, tip 55 should be in physical contact with wall 70 in order to accurately measure distance 72 between sensor 50 and tip 77.

In some embodiments, calibration jig 66 comprises both sensors 77 and 88. The inventor found that by using the scaling factor described above, the distance between sensor 50 and tip 55 can be estimated with improved accuracy.

In the example embodiments of FIG. 2, the distance between sensor 50 and tip 55 is measured along one axis, therefore, the value of distance 72 is a scalar. In other configurations, the techniques described above may be applied to provide a two-dimensional (2D) estimation (e.g., a vector) of the distance, for example, between the position sensor and a selected location in a 2D-shaped device.

This particular configuration of calibration jig 66 is shown by way of example, in order to illustrate certain problems that are addressed by embodiments of the present invention and to demonstrate the application of these embodiments in enhancing the performance of such a position tracking system. Embodiments of the present invention, however, are by no means limited to this specific sort of example system, and the principles described herein may similarly be applied to other sorts of catheterization and position tracking systems that are known in the art.

For example, sensors 77 and/or 88, or other position sensors (not shown) can be fixed at any suitable configuration in fixture 52. Furthermore, the size and shape of calibration jig 66 is designed to fit over assembly 40. In other examples, the configuration of the jig may be different in order to enable calibration of a medical device comprising one or more position sensors and having a different configuration. Moreover, the principles described above may be applied for calibrating other types of position sensors (e.g., other than magnetic-based) using suitable configurations of appliance 46 and calibration jig 66.

Although the embodiments described herein mainly address minimally invasive medical devices comprising position sensors, the methods and systems described herein can also be used in other applications, such as in image guided surgery (e.g., sinuplasty), in implanting procedures having a sensor embedded in an implant, and in various endoscopic procedures such as laryngoscopy.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. An apparatus, comprising:
   (a) a calibration fixture, sized and shaped to fit over a distal-end of a medical probe, such that the distal-end makes physical contact with a wall of the calibration fixture;
   (b) a calibration position sensor, fixed in the calibration fixture at a known position relative to the wall, and configured, in response to sensing a magnetic field, to produce position signals indicative of a given position of the calibration position sensor;
   (c) interface circuitry, which is electrically coupled to the calibration position sensor, and is configured to output the position signals; and
   (d) a processor, which is configured to:
   (i) receive electrical signals indicative of a measured position of a probe position sensor attached to the medical probe,
   (ii) receive the position signals produced by the calibration position sensor, and
   (iii) estimate, based on the electrical signals and the position signals, a distance between the probe position sensor and a tip of the distal-end by subtracting a predetermined distance between the wall and the calibration position sensor from an estimated distance between the calibration position sensor and the probe position sensor.

2. The apparatus according to claim 1, and comprising an additional calibration position sensor, fixed in the calibration fixture at a predefined position relative to the calibration position sensor, and configured, in response to sensing the magnetic field, to produce additional position signals indicative of an additional position of the additional calibration position sensor, wherein the processor is configured to produce, based on the predefined position, the position signals and the additional position signals, a scaling factor for estimating the distance.

3. The apparatus according to claim 1, wherein the interface circuitry is configured to transmit the position signals wirelessly or via an electrical cable coupled to the interface circuitry.

4. The apparatus according to claim 1, and comprising a calibration appliance, which is fixed to the calibration fixture and is configured to produce the magnetic field.

5. The apparatus according to claim 4, wherein the calibration appliance comprises multiple Helmholtz coils, which are configured to produce the magnetic field.

6. The apparatus according to claim 1, wherein the calibration fixture comprises a non-magnetic material and an opening that extends as a hole into the non-magnetic material for receiving the distal-end of the medical probe, wherein the wall is presented by the hole.

7. The apparatus according to claim 6, wherein the hole defines a diameter slightly larger than a diameter of the distal-end of the medical probe.

8. A method for producing a calibration apparatus, the method comprising:
(a) producing a calibration fixture, sized and shaped to fit over a distal-end of a medical probe, such that the distal-end makes physical contact with a wall of the calibration fixture;
(b) fixing in the calibration fixture, at a known position relative to the wall, a calibration position sensor for producing position signals indicative of a given position of the calibration position sensor in response to sensing a magnetic field;
(c) electrically coupling to the calibration position sensor, interface circuitry for outputting the position signals; and
(d) coupling to the interface circuitry a processor for:
(i) receiving electrical signals indicative of a measured position of a probe position sensor attached to the medical probe,
(ii) receiving the position signals produced by the calibration position sensor, and
(iii) estimating, based on the electrical signals and the position signals, a distance between the probe position sensor and a tip of the distal-end by subtracting a predetermined distance between the wall and the calibration position sensor from an estimated distance between the calibration position sensor and the probe position sensor.

9. The method according to claim 8, and comprising fixing in the calibration fixture, at a predefined position relative to the calibration position sensor, an additional calibration position sensor, for producing, in response to sensing the magnetic field, additional position signals indicative of an additional position of the additional calibration position sensor, such that the processor produces, based on (i) the predefined position, (ii) the position signals, and (iii) the additional position signals, a scaling factor for estimating the distance.

10. The method according to claim 8, and comprising fixing the calibration fixture to a calibration appliance that produces the magnetic field.

11. The method according to claim 8, and comprising coupling to the interface circuitry at least one of an electrical cable and a wireless communication device for transmitting the position signals.

12. The method according to claim 8, wherein the calibration fixture comprises a non-magnetic material and an opening that extends as a hole into the non-magnetic material for receiving the distal-end of the medical probe, wherein the wall is presented by the hole.

13. The method according to claim 12, wherein the hole defines a diameter slightly larger than a diameter of the distal-end of the medical probe.

14. A method, comprising:
(a) receiving via a processor, position signals indicative of a given position of a calibration position sensor fixed in a calibration fixture at a known position relative to a wall of the calibration fixture, wherein the calibration fixture is sized and shaped to fit over a distal-end of a medical probe, such that the distal-end makes physical contact with the wall of the calibration fixture;
(b) receiving via the processor, electrical signals indicative of a measured position of a probe position sensor attached to the medical probe, wherein a tip of the distal-end makes physical contact with the wall; and
(c) estimating via the processor, based on the electrical signals and the position signals, a distance between the probe position sensor and the tip of the distal-end, wherein the act of estimating a distance between the probe position sensor and the tip of the distal-end includes subtracting via the processor, a predetermined distance between the wall and the calibration position sensor from an estimated distance between the calibration position sensor and the probe position sensor.

15. The method according to claim 14, further comprising:
(a) receiving via the processor, additional position signals indicative of an additional position of an additional calibration position sensor fixed in the calibration fixture at a predefined position relative to the calibration position sensor; and
(b) producing via the processor, based on the predefined position, the position signals and the additional position signals, a scaling factor for estimating the distance.

16. The method according to claim 14, further comprising selectively inserting the distal-end of the medical probe into the calibration fixture such that the tip of the distal-end makes physical contact with the wall of the calibration fixture.

17. The method according to claim 14, wherein the act of estimating a distance between the probe position sensor and the tip of the distal-end includes:
(a) estimating via the processor, based on the electrical signals and the position signals, the estimated distance between the calibration position sensor and the probe position sensor.

18. The method according to claim 14, further comprising producing a magnetic field, wherein the position signals and the electrical signals are produced in response to the calibration position sensor and the probe position sensor sensing the magnetic field, respectively.

19. The method according to claim 14, wherein the calibration fixture comprises a non-magnetic material and an opening that extends as a hole into the non-magnetic material for receiving the distal-end of the medical probe, wherein the wall is presented by the hole.

20. The method according to claim 19, wherein the hole defines a diameter slightly larger than a diameter of the distal-end of the medical probe.

* * * * *